United States Patent [19]

Mizutani et al.

[11] Patent Number: 4,849,529

[45] Date of Patent: Jul. 18, 1989

[54] METHOD FOR PRODUCTION OF SPIRO-ORTHOCARBONATE

[75] Inventors: Kiyokazu Mizutani; Hitoshi Kato; Kuniko Ogasawara, all of Aichi; Takeshi Endo, Kanagawa, all of Japan

[73] Assignee: Toagosei Chemical Industry, Ltd., Tokyo, Japan

[21] Appl. No.: 4,401

[22] Filed: Jan. 20, 1987

Related U.S. Application Data

[63] Continuation of Ser. No. 581,530, Feb. 21, 1984, abandoned.

[30] Foreign Application Priority Data

Feb. 21, 1983 [JP] Japan .................................. 58-26305

[51] Int. Cl.$^4$ ............................................ C07D 319/14
[52] U.S. Cl. ...................................................... 549/334
[58] Field of Search ........................................ 549/334

[56] References Cited

U.S. PATENT DOCUMENTS

| | | | |
|---|---|---|---|
| 2,606,909 | 8/1952 | Blicke | 549/334 |
| 2,851,469 | 9/1958 | Testard | 549/518 |
| 4,276,223 | 6/1981 | Wu | 549/518 |

FOREIGN PATENT DOCUMENTS

| | | | |
|---|---|---|---|
| 1084733 | 7/1960 | Fed. Rep. of Germany | 549/334 |
| 3225818 | 2/1983 | Fed. Rep. of Germany | |
| 7696 | 2/1971 | Japan | 549/334 |
| 161419 | 12/1981 | Japan | 549/334 |

OTHER PUBLICATIONS

Houben-Weyl, Methoden der Organischen Chemie, (1965), 4th Ed., vol. VI/3, pp. 311-313.
K. Soga et al., Journal of Polymer Science: Polymer Chemistry Edition, vol. 15, (1977), pp. 219-229.
B. Trathnigg et al., Die Angewandte Makromolekulare Chemie, vol. 105, (1982), pp. 1-7, (No. 1647).

*Primary Examiner*—Richard L. Raymond
*Assistant Examiner*—Mark W. Russell
*Attorney, Agent, or Firm*—Sughrue, Mion, Zinn, Macpeak & Seas

[57] ABSTRACT

A method for producing spiro-orthocarbonate compounds is disclosed. The method comprises reacting a cyclic carbonate compound of the following formula with an epoxy compound containing an epoxy group:

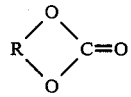

wherein R is an alkylene group or a substituted alkylene group. The disclosed method makes it easy to commercially produce spiro-orthocarbonate compounds in a one stage reaction. The starting materials can be easily handled without any hygienic difficulties and the method can be carried out without entailing any operational difficulties.

14 Claims, 7 Drawing Sheets

METHOD FOR PRODUCTION OF SPIRO-ORTHOCARBONATE

This is a continuation of application Ser. No. 581,530, filed Feb. 21, 1984, now abandoned.

FIELD OF THE INVENTION

This invention relates to a method for the production of spiro-orthocarbonate, and more particularly to a method for the production of spiro-orthocarbonate by the reaction of specific cyclic carbonate compound with an epoxy compound.

BACKGROUND OF THE INVENTION

Spiro-orthocarbonate compounds and methods of making them are known. For example, a method resorting to the reaction of bis(tributyltin)-alkylene glycolates with carbon disulfide disclosed in *Journal of Organic Chemistry*, 35, 2347 (1970) and a method relaying on the reaction of dialkyl-tin cyclic dialkoxides with carbon disulfide disclosed similarly in *Journal of Organic Chemistry*, 36, 1176 (1971) are known for the production of such compounds. The latter method may be expressed by reaction formulas as follows:

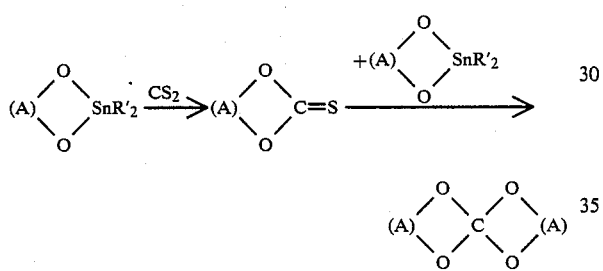

wherein (A) represents a polymethylene group or an alkyl substituent thereof and R' represents an alkyl group.

The above described conventional methods use, as raw materials, organic tin compounds which are not ordinary commercial products and carbon disulfide which is too toxic to permit easy handling. The reactions involved therein are complicated and the products of these reactions are extremely difficult of isolation. Thus, these methods entail various problems. Accordingly, these methods are not feasible for the commercial production of spiroorthocarbonates.

It has been known to produce cyclic acetals by the reaction of aldehydes or ketones and alkylene oxides, as described in G. Willfang, *Ber.* 74, 145 (1941) and M.T. Bogert et al, *J. Am. Chem. Soc.*, 55, 3741 (1933). On the other hand, it has also been known that cyclic carbonates exhibit quite different reactivity and reaction behavior from those of aldehydes or ketones though cyclic carbonates have a carbonyl group as well as aldehydes and ketones. For example, ketones react with mercaptans, amines or hydrogen cyanide to produce mercaptols or cyanohydrines, whereas cyclic carbonates do not react or are decomposed to produce dioxide gas and quite different compounds such as thioethers, β-hydroxyethylamin, etc., and further cyclic carbonates react with phenols, diamines, urea, carboxylic acids, etc., though ketones do not react with such compounds or they react in quite different behavior.

SUMMARY OF THE INVENTION

An object of this invention is to provide a method which is capable of producing a spiro-orthocarbonate without entailing any operational or hygienic difficulty.

As a result of a diligent study in search of an advantageous method for the production of spiro-ortocarbonates, it has now been found that a spiro-orthocarbonate can be very easily produced by the one-stage reaction of a cyclic carbonate (which is easy to handle) with an epoxy compound. This invention has been achieved on the basis of the discovery.

DETAILED DESCRIPTION OF THE INVENTION

Figure 1:
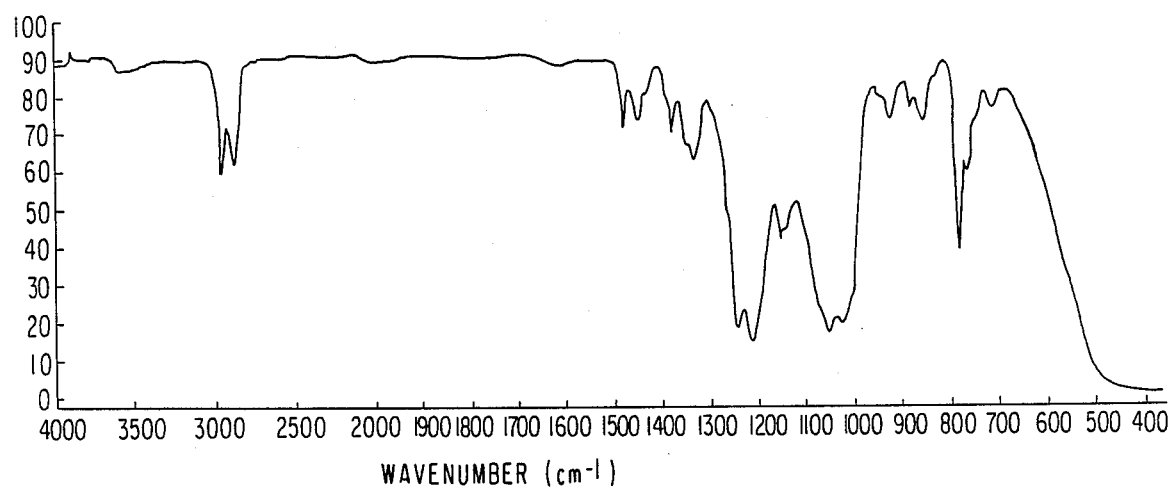
FIGS. 1 and 2 are an IR spectrum and an NMR spectrum, respectively, of 7-chloromethyl-2-methyl-1,4,6,9-tetraoxaspiro[4.4]nonane obtained in Example 1.

Specifically, this invention relates to a method for producing a spiro-orthocarbonate by reacting a cyclic carbonate with an epoxy compound as follows:

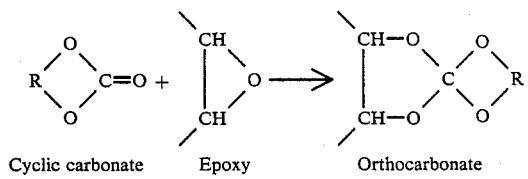

Cyclic carbonate    Epoxy    Orthocarbonate

In this reaction formula, R is an alkylene group represented by $(CH_2)_n$ where n is preferably an integer of 2 to 5, or a substituted alkylene group having an alkyl group, a haloalkyl group, a hydroxyalkyl group, an aryl group, an alkenyl group, an acyloxy group, an alkoxyalkyl group, an aryloxyalkyl group, an aralkoxyalkyl group, some other organic group, a halogen atom or some other atom substitute for at least one of the hydrogen atoms of the aforementioned alkylene group. Of these substituents, a lower alkyl or haloalkyl group having 1 to 5 carbon atoms and a halogen atoms are preferred.

Examples of cyclic carbonates advantageously used as one raw material in the method of this invention include 1,3-dioxolan-2-one, 4-methyl-1,3-dioxolan-2-one, 4-ethyl-1,3-dioxolan-2-one, 4-chloro-1,3-dioxolan-2-one, 4-chloromethyl-1,3-dioxolan-2-one, 4-phenyl-1,3-dioxolan-2-one, 4-hydroxymethyl-1,3-dioxolan-2-one, 4-(2-hydroxyethyl)-1,3-dioxolan-2-one, 4-[(phenylmethoxy)-methyl]-1,3-dioxolan-2-one, 4,4-dimethyl-1,3-dioxolan-2-one, 4,5-dimethyl-1,3-dioxolan-2-one, 4-methyl-5-phenyl-1,3-dioxolan-2-one, 4,4-dichloro-1,3-dioxolan-2-one, 4-chloro-5-(trichloromethyl)-1,3-dioxolan-2-one, 4-methoxy-5-(trichloromethyl)-1,3-dioxolan-2-one, 4-chloro-5-(dichloromethyl)-1,3-dioxolan-2-one, 4,4,5,5-tetramethyl-1,3-dioxolan-2-one, 4-acetyloxy-1,3-dioxolan-2-one, 4-[(2-methyloxyphenoxy)methyl]-1,3-dioxolan-2-one, 1,3-dioxan-2-one, 4-methyl-1,3-dioxan-2-one, 4,4-dimethyl-1,3-dioxan-2-one, 4,4,-diethyl-1,3-dioxan-2-one, 4,6-dimethyl-1,3-dioxan-2-one, 5-ethyl-5-(hydroxymethyl)-1,3-dioxan-2-one, 4,5,5-trimethyl-1,3-dioxan-2-one, 4,4,6,6-tetramethyl-1,3-dioxan-2-one, 1,3-dioxepan-2-one. Of these, 1,3-dioxolan-2-one, 4-methyl-1,3-dioxolan-2-one, 4-chloromethyl-1,3-dioxolan-2-one and 1,3-dioxan-2-one are particularly preferred.

Epoxy compounds which can be used as the other raw material are enumerated in (1) through (8) below:

(1) Glycidyl ether or $\beta$-methylglycidyl ether [hereinafter these two compounds will be collectively referred to as "($\beta$-methyl)glycidyl ether"]and polyglycidyl ether or poly($\beta$-methylglycidyl) ether [hereinafter these two compounds will be collectively referred to as "poly(($\beta$-methyl)glycidyl) ether"]etc., which are obtained by the reaction of phenol type compounds such as 2,2-bis(4'-hydroxyphenyl) propane (generally called as "bisphenol A"), halogenated bisphenol A, bis(4-hydroxyphenyl)methane (generally called as "bisphenol F"), resorcinol, tetrahydroxyphenyl methane, novolak type polyfunctional phenols condensed from phenol or cresol with formalin, phenol, cresol and t-butylphenol, with epichlorophydrin or $\beta$-methylepichlorohydrin [hereinafter these two compounds will be collectively referred to as "($\beta$-methyl)epichlorohydrin".];

(2) ($\beta$-Methyl)glycidyl ether, poly(($\beta$-methyl)glycidyl) ether, etc. obtained by the reaction of alcohols such as butyl alcohol, allyl alcohol, ethylene glycol, polyethylene glycol, 2,2-bis(4'-hydroxycyclohexyl)propane, glycerin and 1,1,1-trimethylolpropane with ($\beta$-methyl)epichlorophydrin;

(3) ($\beta$-Methyl)glycidyl ester, poly(($\beta$-methyl)glycidyl) ester, etc. obtained by the reaction of carboxyl groupcontaining compounds such as benzene monocarboxylic acid, adipic acid, sebasic acid, phthalic acid, hexahydrophthalic acid and tetrahydrophthalic acid with ($\beta$-methyl)epichlorophydrin;

(4) Epoxidized olefins, epoxidized polybutadiene, epoxidized vegetable oils, epoxidized cyclopentadiene, etc;

(5) Nitrogen-containing epoxy compounds such as aniline-modified epoxy compounds and nitrogen-containing heterocyclic epoxy compounds obtained from isocyanuric acid epoxide, hydantoin derivatives or imidazoline derivatives;

(6) Butadiene monoxide, stryrene oxide, etc. obtained from mono-unsaturated compounds;

(7) Epihalohydrins such as epichlorohydrin and epichlorohydrin, alkylene oxides such as propylene oxide and $\alpha$-butylene oxide, etc.; and (8) Alicyclic epoxy resins having, on average, at least one end-epoxy group in its molecule such as Chissonox 201, 221, 289, 206, 207 and 1222 (products of Chisso Co., Ltd.) and Araldite CY-175, CY-176, CY-178 and CY-179 (products of Ciba Products Co., Ltd.) which are synthesized by oxidizing intramolecular double bonds.

Commercially available epoxy resins are preferably used in the producton of spiro-orthocarbonates which are useful raw materials for the preparation of adhesives, paints, molding materials, etc. Bisphenol A type epoxy resins are particularly preferred. Further, novolak type epoxy resins and bromium-containing epoxy resins may be used to increase the heat resistance and fire retardance of spiro-orthocarbonates. Taking account of diluents used in the preparation of adhesives, paints, etc., or the production of spiro-orthocarbonates as an intermediate material suitable for the preparation of 6-membered ring products, low molecule weight epoxy compounds are preferably used. From the above aspects, preferred epoxy compounds include glycidyl ethers of phenol; polyglycidyl ethers of a bisphenol A type epoxy resin, a hydrogenated bisphenol A type epoxy resin, an alicyclic epoxy resin or a novolak type polyfunctional phenol obtained by the condensation of phenol or cresol with formaldehyde; epichlorohydrin; epibromohydrin; and propylene oxide.

The reaction can be performed with or without a solvent, but in some cases the reaction proceeds smoothly using a solvent. The solvent is not specifically limited as long as it is inert in the reaction system. Examples of solvents include toluene, xylene, methylene chloride, tetrahydrofuran and dioxane.

The reaction is carried out in the presence of a catalyst such as Lewis acids, e.g., $BF_3$, $AlCl_3$, $AlBr_3$, $SnCl_4$, $SnBr_4$, $TiCl_4$, $FeCl_3$, $SbCl_5$, $ZnCl_2$, $SbCl_3$, etc., coordinated compounds of Lewis acids, e.g., $BF_3OET_2$, $SnCl_4(OET_2)_2$, etc. and protonic acids, e.g., p-toluene sulfonic acid, sulfuric acid, etc. Of these catalyst, Lewis acids and coordinated compounds of Lewis acids are preferably used. The amount of the catalyst to be used is generally in the range of 0.01 to 5 wt %, preferably 0.02 to 3 wt %, based on the amount of the compounds used as the raw materials. Although the reaction temperature is not specifically limited, it is generally 0° C. to 60° C., preferably 0° C. to 40° C.

The equivalent ratio of the epoxy group contained in the epoxy compound to the cyclic carbonate and the amount of the solvent are not specifically limited. Generally, however, the equivalent ratio of the epoxy group to the cyclic carbonate is in the range of 0.2 to 10, preferably 0.2 to 3, and the amount of the solvent is in the range of 0.1 to 20, preferably 0.2 to 10, based on the total weight of the epoxy compound and the cyclic carbonate.

The extent to which the reaction has proceeded can be easily found out by analyzing the reaction solution by gas or liquid-chromatography.

The spiro-orthocarbonate compound thus produced can be isolated generally by inactivating the catalyst with a base and subsequently separating the compound from the reaction system by vacuum distillation, sublimation or recrystallization, depending on the physical properties of the produced compound.

Alternatively, the isolation of the spiro-orthocarbonate compound may be accomplished by adding to the reaction solution an aqueous alkali solution such as an aqueous sodium hydroxide solution to decompose unreacted cyclic carbonate, allowing the reaction system to separate into a water layer and an organic layer, subsequently washing the organic layer with water, and dehydrating the washed organic layer (e.g., with magnesium sulfate), and removing the solvent. Further, the isolation of the spiro-orthocarbonate compound may be effected by removing the solvent from the reaction solution and subjecting the resultant residue to vacuum distillation, sublimation or recrystallization, depending on the physical properties of the compound.

In accordance with the present invention, the useful spiro-orthocarbonate can be easily and efficiently produced in a simple operation by a one-stage reaction from raw materials which are quite easy to handle.

The method of this invention will be described in more detail below with reference to the following examples. However, the scope of this invention is not limited to this example.

EXAMPLE 1

A 1 l four-necked flask equipped with a stirrer, a condenser, a thermometer and a dropping funnel was charged with 200 ml of methylene chloride and 40.8 g (0.4 mol) of 4-methyl-1,3-dioxolan-2-one. The reaction system was cooled to about 25° C. with a water bath. After adding 0.4 ml of $BF_3OEt_2$ thereto, a solution of 44.4 g (0.48 mol) of epichlorohydrin in 200 ml of methylene chloride was added dropwise thereto over a period of about one hour with stirring. The reactants were kept at about 25° C. for four hours for further reaction.

Then, 0.8 ml of triethylamine was added to the reaction solution to inactivate the catalyst. The reaction solution was washed once with 200 ml of 8% aqueous NaOH solution. The organic layer consequently formed was washed twice with 50 ml of distilled water and then dehydrated with $MgSO_4$.

Subsequently, the resultant dehydrated organic layer was treated with a rotary evaporator to remove the solvent and thereafter subjected to vacuum distillation. At boiling points of 93–95° C./1.5 mmHg, there was obtained 21.6 g (28% in yield) of 7-chloromethyl-2-methyl-1,4,6,9-tetraoxaspiro[4.4]nonane.

The physical constants of this compound were as follows.

Figure 2:
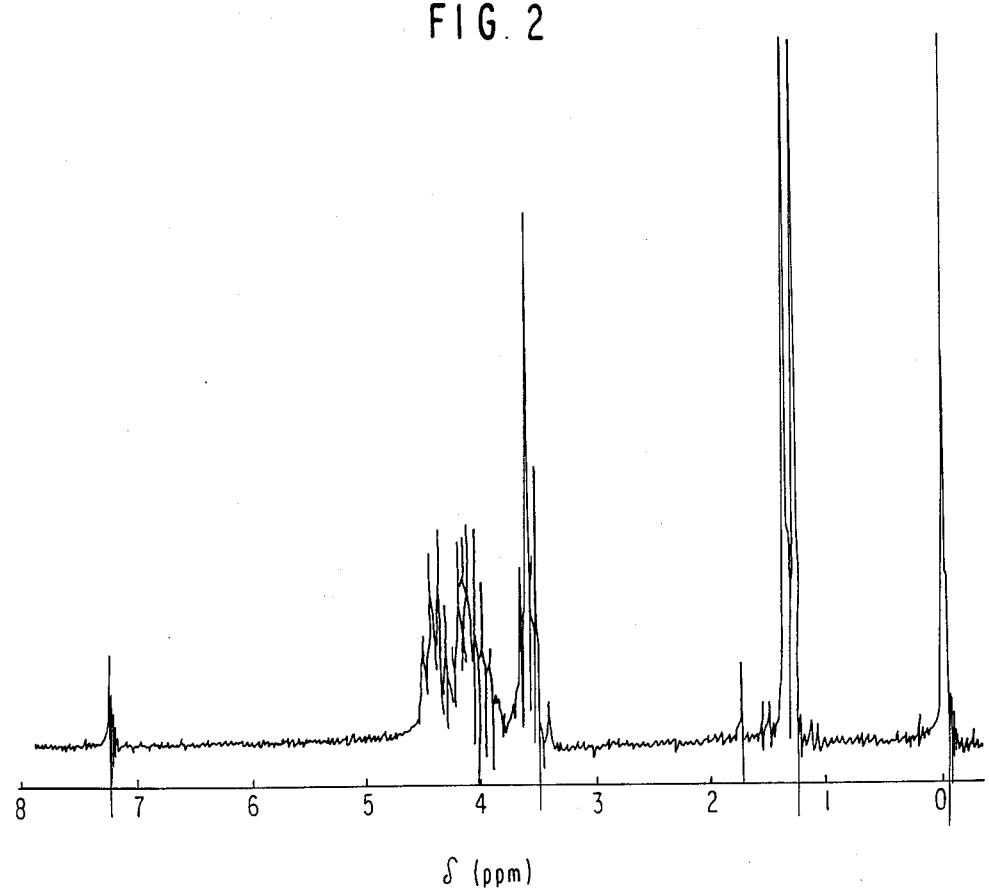

Boiling point: 93 to 95° C./1.5 mmHg
IR: 1243 $cm^{-1}$, 1053 $cm^{-1}$ (C—O—C) (See FIG. 1)
NMR: δ (ppm) (in $CDCl_3$) (See FIG. 2); 3.8 to 4.6 (5H, 2CH—O, 3H of $CH_2$—O); 3.4 to 3.8 (3H, $CH_2$—Cl, 1H of $CH_2$—O); 1.2 to 1.5 (3H, d, C—$CH_3$)
Mass analysis: Parent peak (P-1) (m/e); 193

EXAMPLE 2

A four-necked flask equipped with a stirrer, a condenser, a thermometer and a dropping funnel was charged with 600 ml of methylene chloride and 303.0 g (3.44 mol) of 1,3-dioxolan-2-one. The reaction system was cooled to 15° C., and 1.61 ml of boron trifluoride etherate was added thereto. While keeping the reaction system at 15° C., a solution of 159.2 g (1.72 mol) of epichlorohydrin in 500 ml of methylene chloride was added dropwise to the reaction system over a period of four hours and the reaction was further continued for four hours.

Then, 4 ml of triethylamine was added to stop the reaction, followed by washing the reaction solution with 1500 g of a 10% aqueous NaOH solution to remove the excess 1,3-dioxolan-2-one. After washing three times with water, the resulting solution was subjected to dehydration and a solvent-removal treatment to obtain a concentrated liquid. Then, the liquid was subjected to vacuum distillation, whereby 133.3 g (43% in yield) of 2-chloromethyl-1,4,6,9-tetraoxaspiro-[4.4]nonane. At the asme time, 11.3 g (5.7% in yield) of 2,7-dichloromethyl-1,4,6,9-tetraoxaspiro[4.4]nonane was also obtained.

The physical constants of the compounds were as follows.

Figure 3:
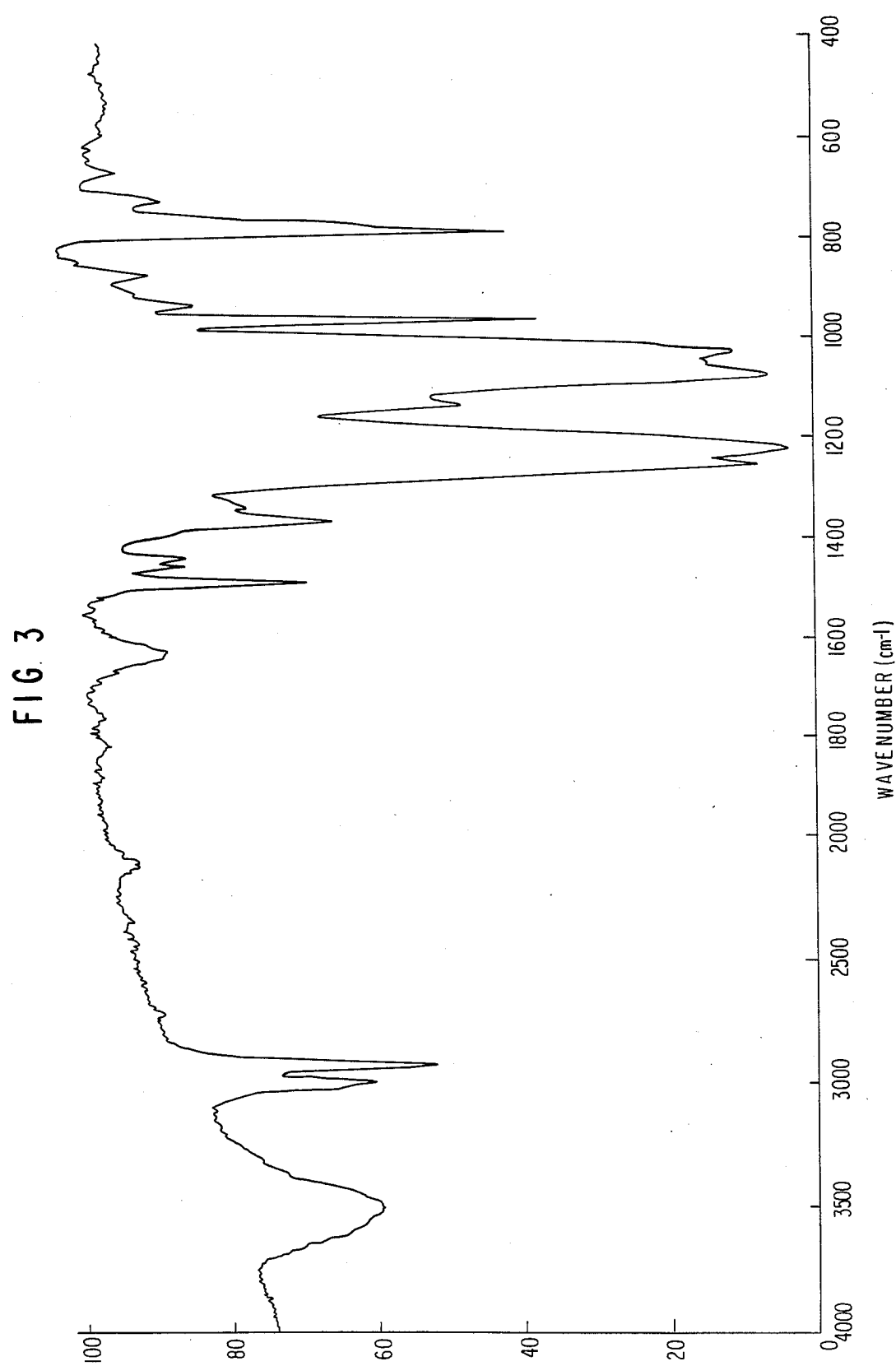
FIGS. 3 and 4 are an IR spectrum and an NMR spectrum, respectively, of 2-chloromethyl-1,4,6,9-tetraoxaspiro[4.4]nonane obtained in Example 2.
Figure 4:
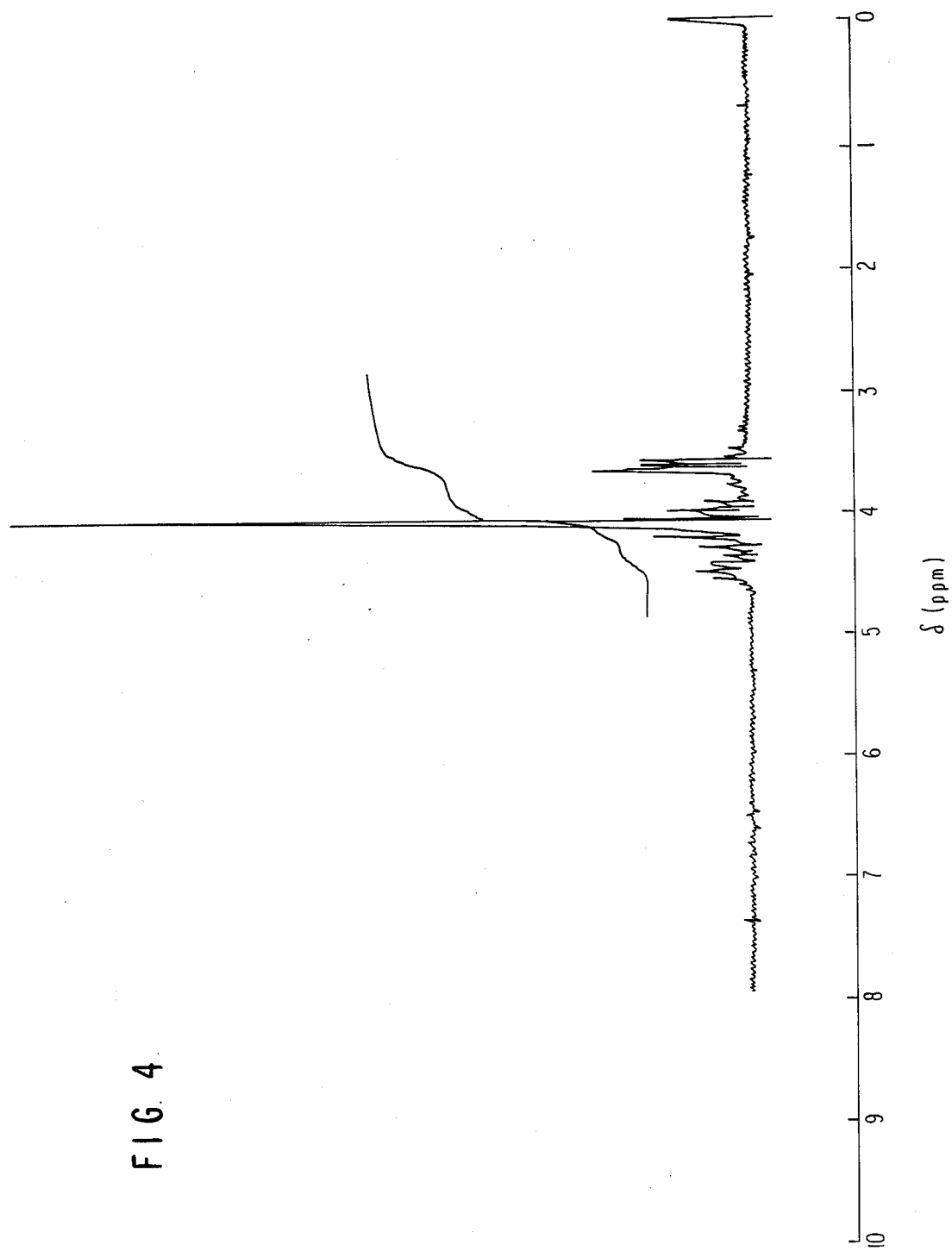

(i) 2-chloromethyl-1,4,6,9-tetraoxaspiro[4.4]nonane:
Boiling point: 99 to 116° C./1 mmHg
IR: 1220 $cm^{-1}$, 1075 $cm^{-1}$ (C—O—C), 790 $cm^{-1}$ (C—Cl) (See FIG. 3)
NMR: δ (ppm) (in $CDCl_3$) (See FIG. 4); 3.5 to 3.8 (2H, $ClCH_2$—); 3.8 to 4.6 (7H, protons of the methine and methylene groups bonded to the oxygen atoms)

Figure 5:
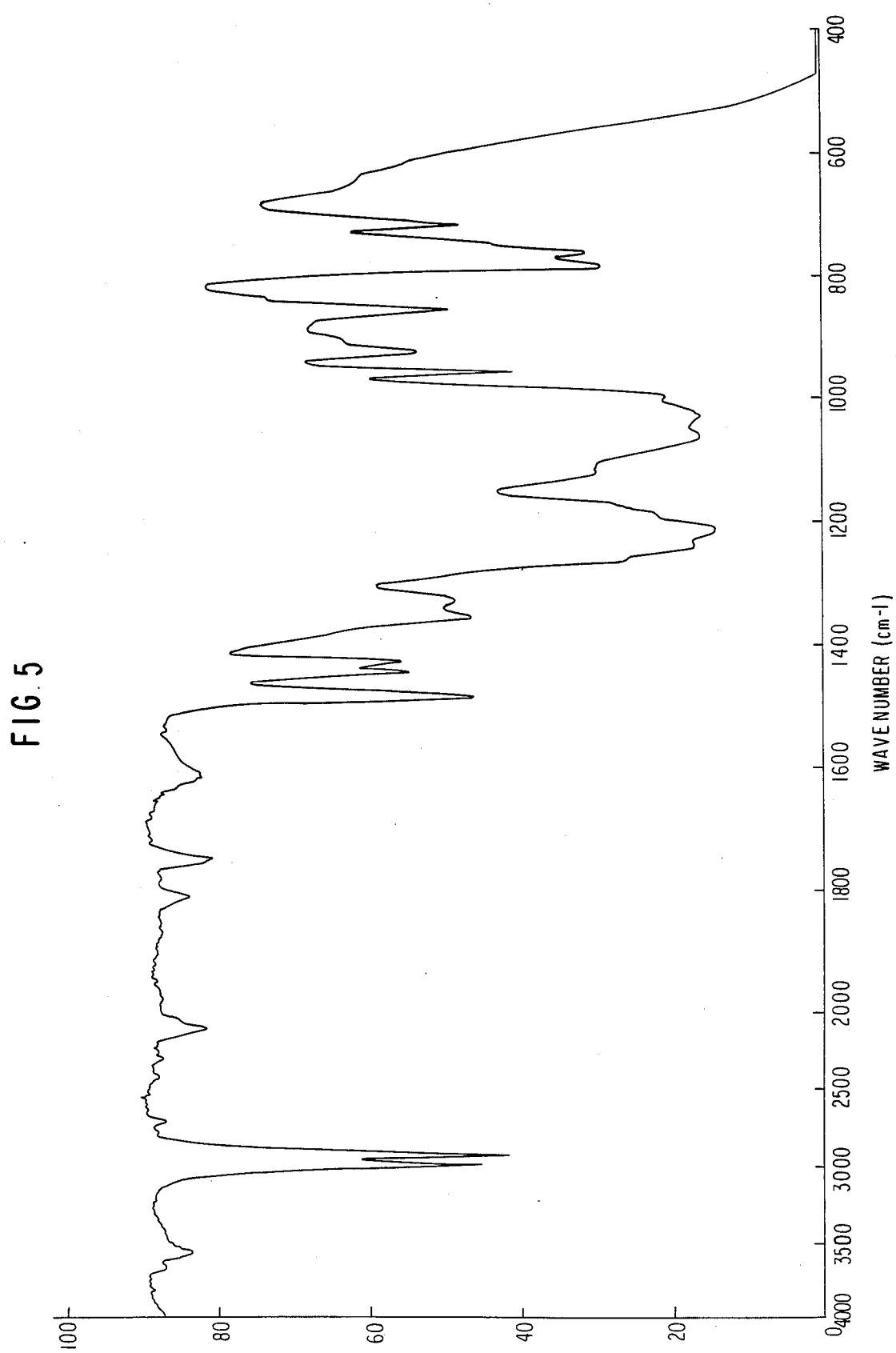
FIGS. 5 and 6 are an IR spectrum and an NMR spectrum, respectively, of 2,7-dichloromethyl-1,4,6,9-tetraoxaspiro[4.4]nonane obtained in Example 2.
Figure 6:
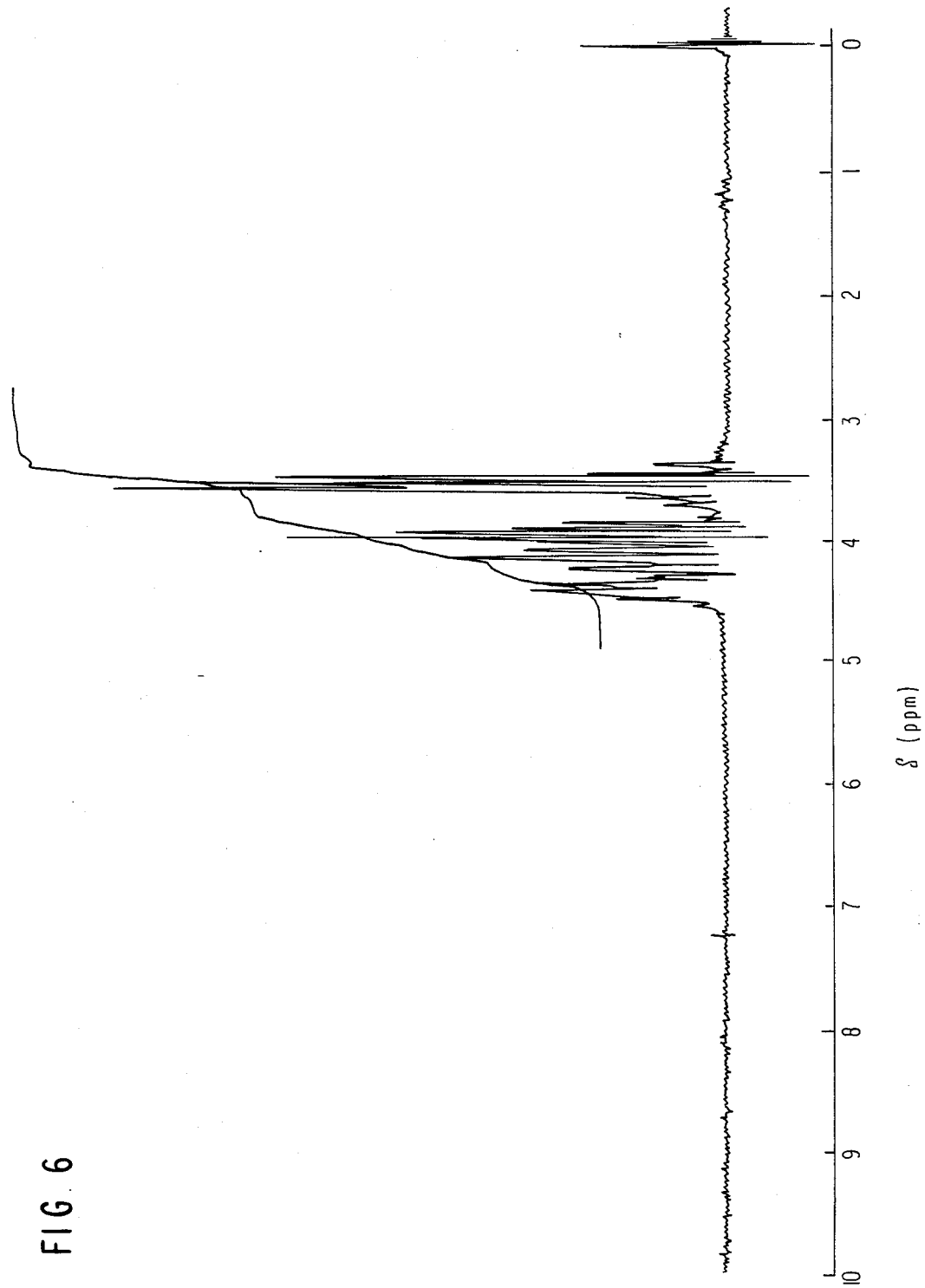

(ii) 2,7-Dichloromethyl-1,4,6,9-tetraoxaspiro[4.4]nonane
Boiling point: 117° C./1 mmHg
IR: 1210 $cm^{-1}$, 1060 $cm^{-1}$ (C—O—C), 790 $cm^{-1}$ (C—Cl) (See FIG. 5)
NMR: δ(ppm) (in $CDCl_3$) (See FIG. 6); 3.3 to 3.8 (4H, 2$ClCH_2$—); 3.8 to 4.6 (6H, protons of the methine and methylene groups bonded to the oxygen atoms)

EXAMPLE 3

A four-necked flask equipped with a stirrer, a condenser, a thermometer and a dropping funnel was charged with 150 ml of methylene chloride and 88.1 g (1.00 mol) of 1,3-dioxolan-2-one. The reaction system was cooled to 15° C., and 0.47 ml of boron trifluoride etherate was added thereto. While keeping the reaction system at 15° C., a solution of 29.0 g (0.50 mol) of propylene oxide in 120 ml of methylene chloride was added dropwise to the reaction system over a period of 1.5 hours, and the reaction was further continued for 3.5 hours at 20° C.

Then, 1 ml of triethylamine was added to stop the reaction. The resulting reaction solution was analyzed by gas chromatography and mass spectrography, and it was revealed that a compound having the parent peak (m/e) of 146 which corresponds to the molecular weight of 2-methyl-1,4,6,9-tetraoxaspiro[4.4]nonane was produced and that its yield was about 65% (calculated from its peak area measured by gas chromatography).

EXAMPLE 4

4-methyl-1,3-dioxolan-2-one and propylene oxide were reacted in a similar manner to the procedure of Example 2, whereby 2,7-dimethyl-1,4,6,9-tetraoxaspiro[4.4]nonane was obtained in yield of about 70%.

The production of 2,7-dimethyl-1,4,6,9-tetraoxaspiro[4.4]nonane was confirmed by mass spectrography (parent peak (m/e):160) and the yield was calculated from the results obtained by gas chromatography.

EXAMPLE 5

A four-necked flask equipped with a stirrer, a condenser, a thermometer and a dropping funnel was charged with 30 ml of methylene chloride and 4.59 g (0.045 mol) of 4-methyl-1,3-dioxolan-2-one. The reaction system was cooled to 10° C., and 28 $\mu$l of boron trifluoride etherate was added thereto. While keeping the reaction system at 10° C., a solution of 5.18 g (0.03 eq) of Epototo YD-8125 (a diglycidyl ether obtained from bisphenol A, produced by Toto Kasei Co.) in 20 ml of methylene chloride was added dropwise to the reaction system over a period of one hour and the reaction was further continued for four hours at 15° C.

Then, 60 $\mu$l of triethylamine was added to stop the reaction, followed by washing the reaction solution with 20 g of a 10% aqueous NaOH solution to remove the excess 4-methyl-1,3-dioxolan-2-one. After washing twice with water, the resulting solution was subjected to dehydration to obtain about 20 ml of a concentrated liquid. Then, the liquid was poured into 200 ml of acetone and subjected to filtration. The filtrate was evaporated to dryness to obtain 3.1 g of white powder. As a result of the instrumental analysis, it was found that about 50% of the epoxy groups of the diglycidyl ether used herein were converted to the spiro-orthocarbonate structure and that the resulting spiro-orthocarbonate had the chemical structure shown in the NMR data below.

The physical constants of the compound were as follows.

Figure 7:
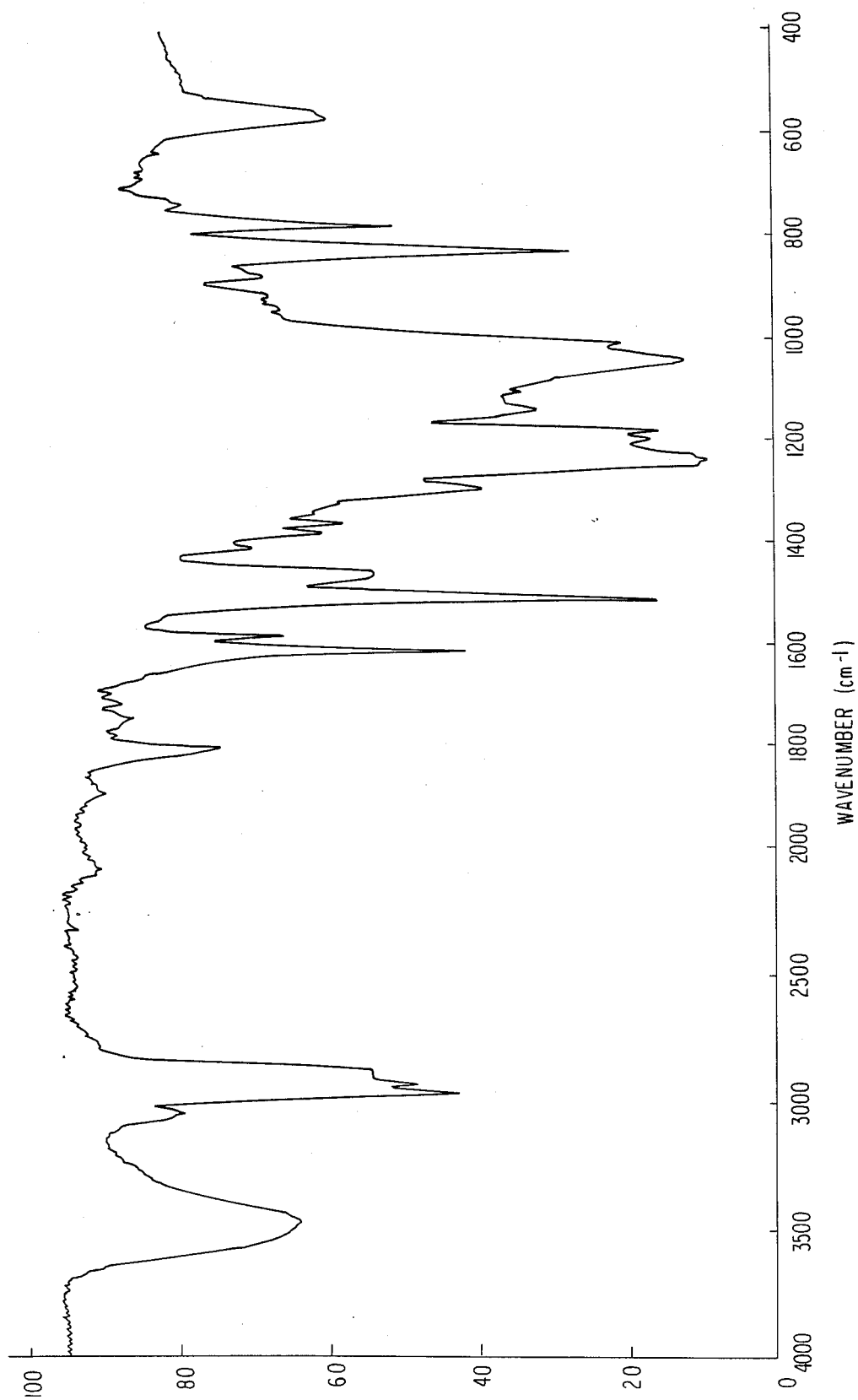
FIGS. 7 and 8 are an IR spectrum and an NMR spectrum, respectively, of the spiro-orthocarbonate compound obtained in Example 5.
Figure 8:
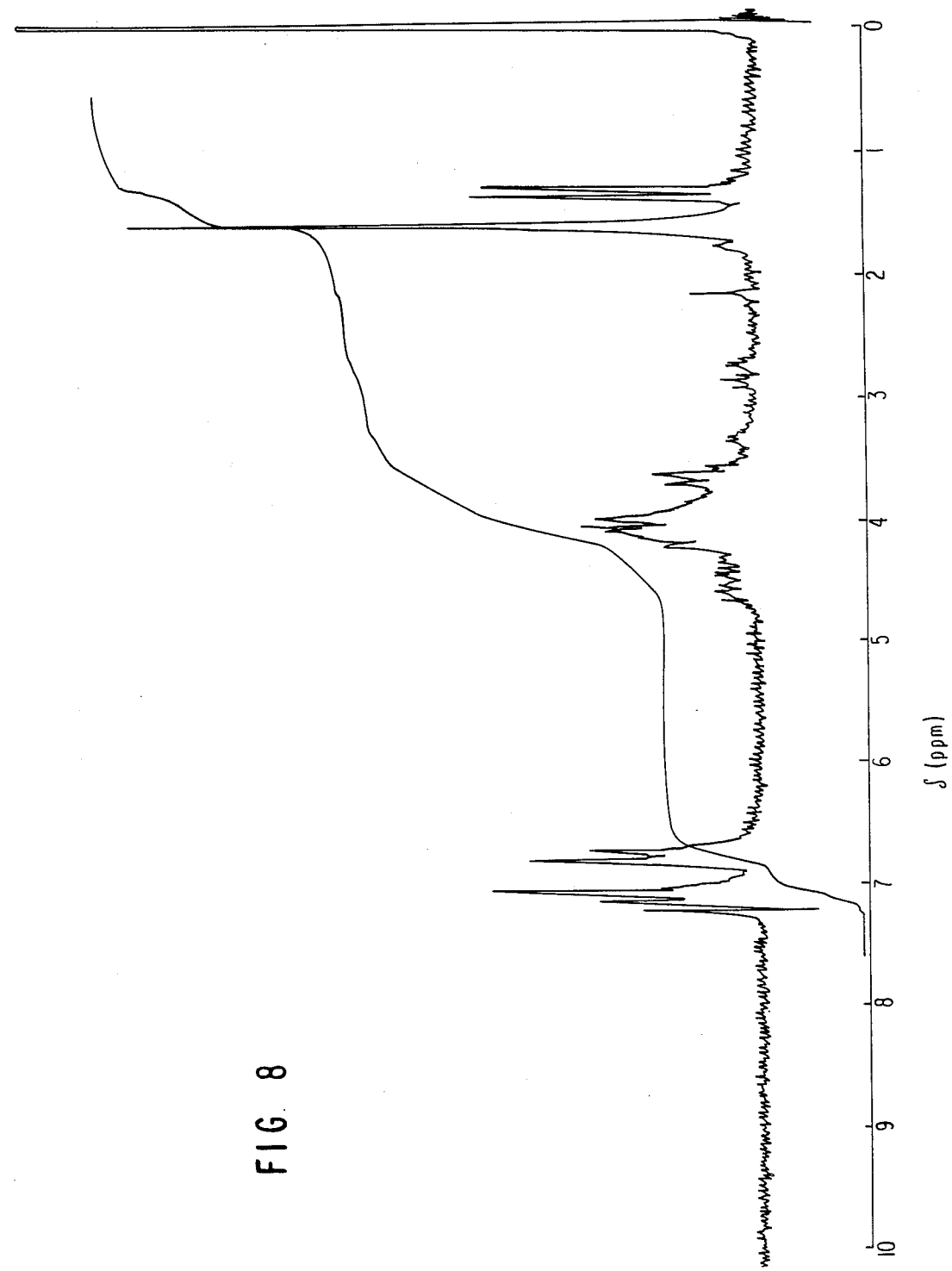

IR: 1240 cm$^{-1}$, 1040 cm$^{-1}$ (C—O—C) (See FIG. 7)
NMR: (in CDCl$_3$) (See FIG. 8)

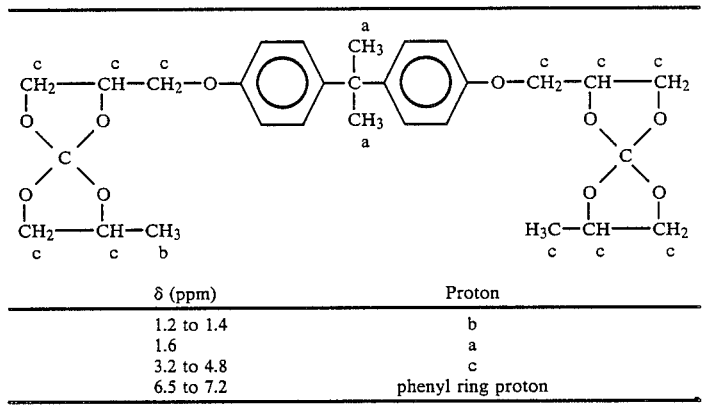

| δ (ppm) | Proton |
|---|---|
| 1.2 to 1.4 | b |
| 1.6 | a |
| 3.2 to 4.8 | c |
| 6.5 to 7.2 | phenyl ring proton |

What is claimed is:

1. A method for producing a spiro-orthocarbonate compound, comprising:
reacting a cyclic carbonate compound represented by the following formula in the presence of a catalyst with one member selected from the group consisting of an epihalohydrin, an alkylene oxide and a glycidyl ether obtained by reacting an epihalohydrin with 2,2-bis(4'-hydroxyphenyl)-propane or phenol:

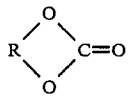

wherein R is an ethylene group, an ethylene group substituted with one or more alkyl groups having 1–5 carbon atoms, an ethylene group substituted with one halogen atom or one haloalkyl group having 1 to 5 carbon atoms, or an ethylene group substituted with one or more alkyl groups having 1 to 5 carbon atoms and one halogen atom or one haloalkyl group having 1 to 5 carbon atoms.

2. A method as claimed in claim 1 wherein the cyclic carbonate compound is selected from the group consisting of 1,3-dioxolan-2-one, 4-methyl-1,3-dioxolan-2-one and 4-chloromethyl-1,3-dioxolan-2-one.

3. A method as claimed in claim 1, wherein the catalyst is selected from the group consisting of Lewis acids, coordinated compounds of Lewis acids, and protonic acids.

4. A method as claimed in claim 1, wherein the catalyst is selected from the group consisting of Lewis acids and coordinated compounds of Lewis acids.

5. A method as claimed in claim 1, wherein the catalyst is present in an amount in the range of 0.01 to 5 wt % based on the amount of cyclic carbonate compound and epoxy compound.

6. A method as claimed in claim 1, wherein the catalyst is present in an amount in the range of 0.02 to 3 wt % based on the amount of said cyclic carbonate compound and said one member.

7. A method as claimed in claim 1, wherein the reaction is carried out at a temperature in the range of 0° C. to 60° C.

8. A method as claimed in claim 1, wherein the reaction is carried out at a temperature in the range of 0° C. to 40° C.

9. A method as claimed in claim 1, wherein the equivalent ratio of an epoxy group in said epihalohydrin, alkylene oxide or clycidyl ether to the cyclic carbonate is in the range of 0.2 to 10.

10. A method as claimed in claim 1, wherein the equivalent ratio of an epoxy group in said epihalohydrin, alkylene oxide or glycidyl ether to the cyclic carbonate is in the range of 0.2 to 3.

11. A method as claimed in claim 1, wherein the reaction is carried out in the presence of a solvent and the solvent is present in the range of 0.1 to 20 parts by weight based on the total weight of the epihalohydrin, alkylene oxide or glycidyl ether and the cyclic carbonate compound.

12. A method as claimed in claim 1, wherein the reaction is carried out in the presence of a solvent and the solvent is present in the range of 0.2 to 10 parts by weight based on the total weight of the epihalohydrin, alkylene oxide or glycidyl ether and the cyclic carbonate compound.

13. A method as claimed in claim 1, wherein the spiro-orthocarbonate compound is 7-chloromethyl-2-methyl-1,4,6,9-tetraoxaspiro[4.4]nonane, 2-chloromethyl-1,4,6,9-tetraoxaspiro[4.4]nonane, 2-methyl-1,4,6,9-tetraoxaspiro[4.4]nonane, 2,7-dichloromethyl-1,4,6,9-tetraoxaspiro[4.4]nonane, 2,7-dimethyl-1,4,6,9-tetraoxaspiro[4.4]nonane or a spiro-orthocarbonate produced by reacting 4-methyl-1,3-dioxan-2-one with the glycidyl ether.

14. A method as claimed in claim 1, wherein the alkylene oxide is propylene oxide or α-butylene oxide.

* * * * *